United States Patent [19]

Edenbaum et al.

[11] Patent Number: 5,318,504
[45] Date of Patent: Jun. 7, 1994

[54] DRY SURFACE CAST WITH WATER POUCH

[75] Inventors: Martin Edenbaum, Princeton Junction, N.J.; James L. Clark, Berwyn, Pa.

[73] Assignee: Carapace, Inc., Tulsa, Okla.

[21] Appl. No.: 788,567

[22] Filed: Nov. 6, 1991

Related U.S. Application Data

[63] Continuation-in-part of Ser. No. 700,555, May 15, 1991, Pat. No. 5,171,208.

[51] Int. Cl.⁵ .............................................. A61F 5/04
[52] U.S. Cl. ........................................ 602/8; 602/6
[58] Field of Search .............. 128/877, 878; 604/368, 604/369, 378; 602/6, 7, 8, 9, 12

[56] References Cited

U.S. PATENT DOCUMENTS

| | | | |
|---|---|---|---|
| 4,537,184 | 8/1985 | Williams | 602/8 |
| 5,016,622 | 5/1991 | Norvell | 602/7 |
| 5,027,803 | 7/1991 | Scholz | 602/8 |

*Primary Examiner*—Robert A. Hafer
*Assistant Examiner*—David J. Kenealy
*Attorney, Agent, or Firm*—Head & Johnson

[57] ABSTRACT

A unitary cast or splint forming device which has a layer of cast forming material contained within a water retaining pouch so that water added to the pouch does not wet the exterior. Padded and patient contact layers may be applied to the outside of the pouch.

1 Claim, 3 Drawing Sheets

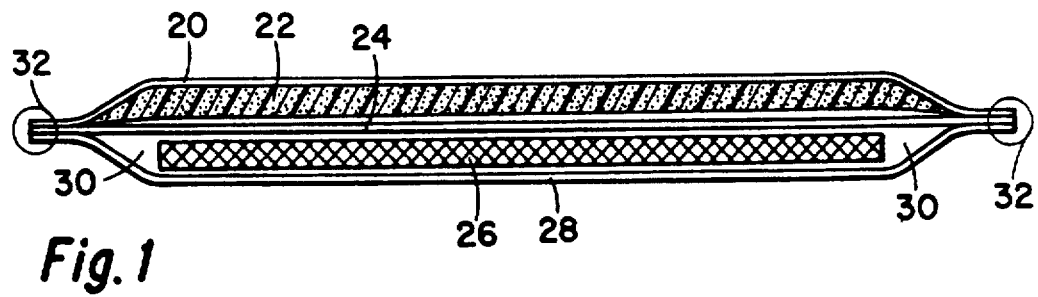
Fig. 1
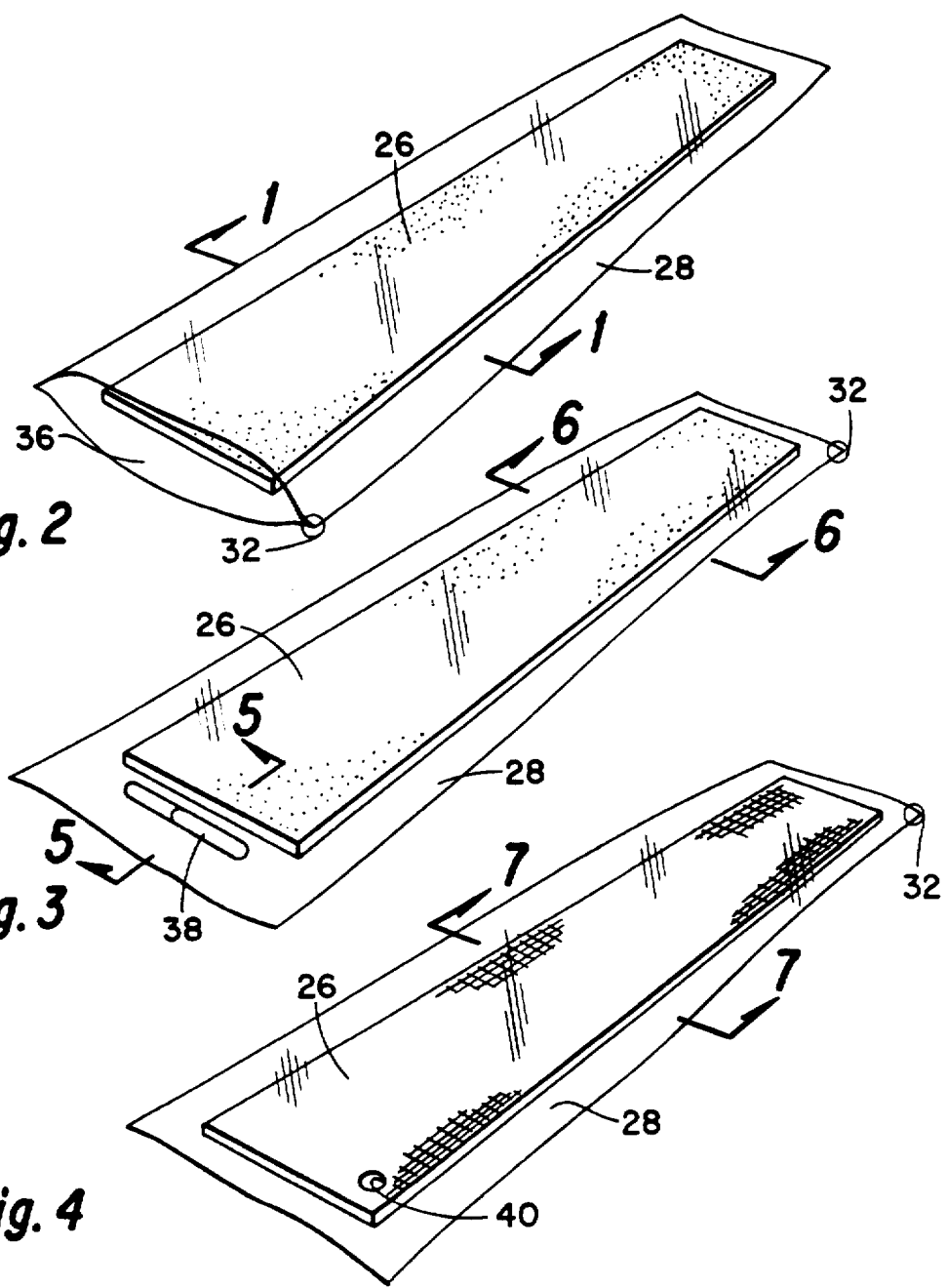
Fig. 2
Fig. 3
Fig. 4

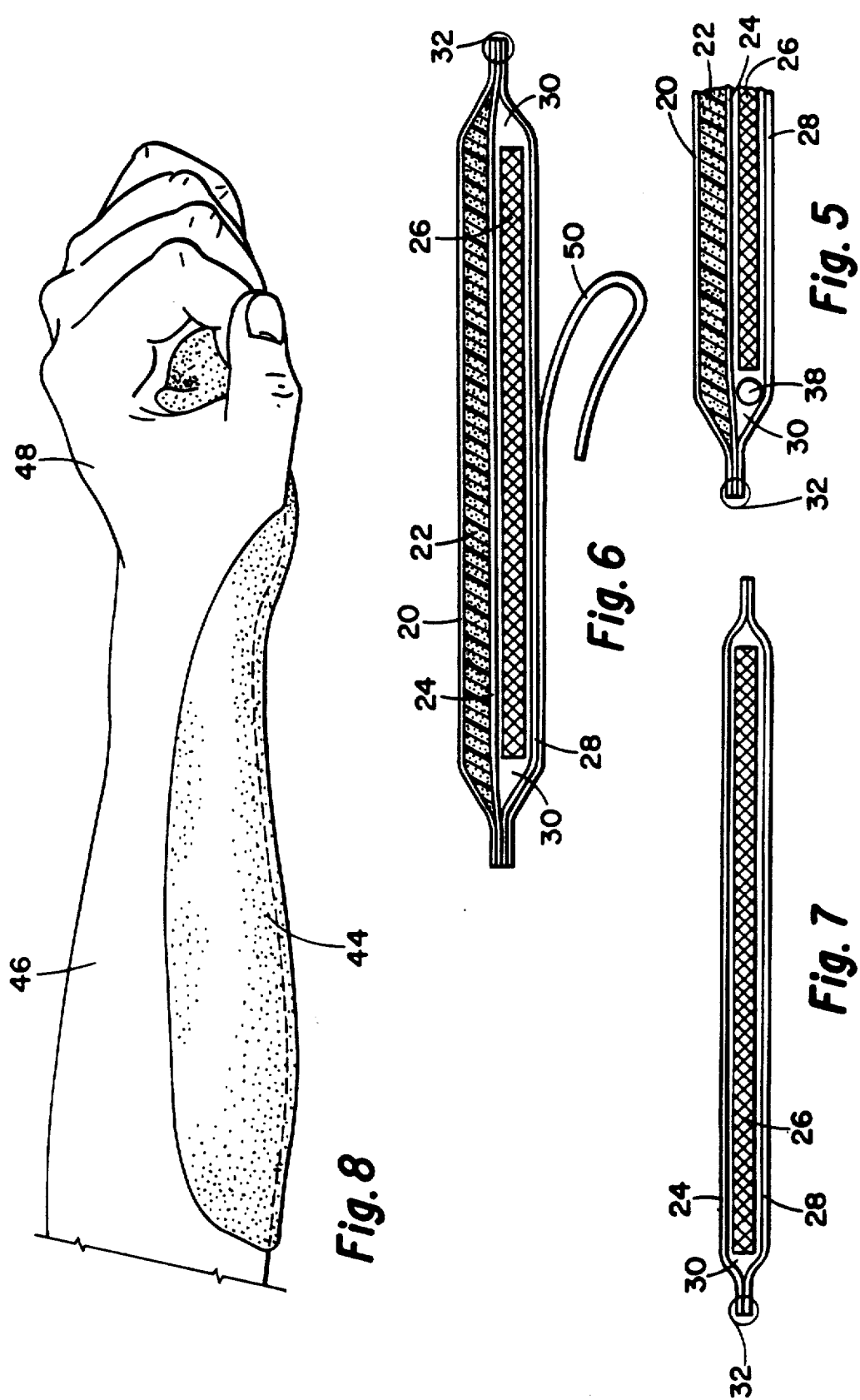

DRY SURFACE CAST WITH WATER POUCH

CROSS REFERENCE TO RELATED APPLICATIONS

This application is a continuation-in-part of application Ser. No. 7/700,555, CASTING OR SPLINTING DEVICE AND METHOD OF MAKING SAME, filed May 15, 1991 now U.S. Pat. No. 5,171,208. All information in the parent application (Ser. No. 07/700,555) now U.S. Pat. No. 5,171,208 is hereby specifically incorporated by reference into this current application.

BACKGROUND OF THE INVENTION

1. Field of the Invention

This invention relates to the field of medical casting and splinting devices. More specifically it relates to those devices which maintain a dry exterior surface.

2. Description of the Related Art

Casts and splints have traditionally been made by coating or impregnating a substrate, usually fabric, such as gauze, mesh, fiberglass or the like with a dry casting material such as plaster of Paris or various resins. The coated substrate is then dipped in water, to initiate the "setting" of the casting material; squeezed or wrung out to express excess water; placed on the appropriate part of the patient; and allowed to dry or "cure."

This process is often very messy, time consuming, requires multiple supplies, and considerable skill. Wet casting material gets on everything from hands, clothes, patient, floor, furniture and the like. Usually the person applying the cast or splint wears gloves and protective clothes and often uses a special "casting" room. If colored compounds are used messy stains may result, and if resins are used, a detackifier may be necessary. Often, a protective layer of material is placed on the patient to protect the skin (see U.S. Pat. No. 4,193,395, which covers the body part with stockinette).

Some casting devices have been described (U.S. Pat. Nos. 4,235,228, 4,442,833, 4,454,874, 4,628,917, 4,770,299, 4,869,046, 4,899,738) which enclose the casting material in sleeves or coverings of various materials so that direct contact with the casting material is not necessary.

Even those devices that enclose the casting material still require immersing the device in water, wringing, and applying. This results in a wet layer of material in direct contact with the patient's skin, which may be uncomfortable and irritating and can, in time, cause maceration and sloughing of the skin. This also requires a ready source of water, which may not be available in some circumstances.

Some devices have tried placing a totally moisture impervious layer next to the skin (U.S. Pat. No. 4,454,874). This may keep moisture from the casting material from contacting the skin. However, it traps moisture that is normally released from the skin in sweating and respiration of the skin, and this builds up under the impervious layer and may cause tissue damage, odor and the like. Other, non-unitary, devices have used a separate dry pad or layer to be applied to the patient or adhered to the casting device after the casting device or material is wetted (U.S. Pat. Nos. 4,193,395 and 4,628,917). These latter devices require more than one component, and adhesives usually do not hold well in a moist environment and may restrict respiration of vapor.

Other devices have been described which use hydrophobic material on the patient contact side, but which still require immersing the device. The immersion and "squeezing" of the device results in water being trapped or retained in the spaces of the hydrophobic material which then presents a wet surface to the patient and may trap moisture next to the patient (U.S. Pat. Nos. 4,770,299, 4,869,046, 4,899,738).

SUMMARY OF THE INVENTION

It is an object of this invention to provide a unitary casting or splinting device that presents a dry, or relatively dry, surface to the patient when applied.

It is a further object of this invention to provide a dry patient contact layer that will allow water vapor passage.

It is yet another object of this invention to provide a self-contained (unitary) device that will not (in some embodiments) require an external source of water.

It is another object of this invention to provide a device in which the casting material is enclosed in a pouch, so there is no direct contact (of the casting material) with either the patient or the person applying the cast and there is no need for detackifiers.

In the preferred embodiment, the device is formed of five layers in essentially laminar and parallel configuration (like the layers or tiers of a sandwich): a patient contact layer, a padded layer, an inner liquid containment layer, a casting material layer, and an outer liquid containment layer. In addition, the inner and outer liquid containment layers define a space (a pouch) between them which holds the casting material layer and also holds or receives the water that activates the casting material. The various layers are fastened together (usually by sealing around the edges) to form a unitary device.

In one embodiment, the pouch (space between the inner and outer liquid containing layers) holds the dry casting material and also has a reservoir which retains and holds water until it is opened or ruptured to release the water into the pouch space and activate the casting material. In this embodiment, the device is totally self-contained and no external source of water is needed.

In another embodiment, the pouch is open on one end (i.e., sealed on three sides) so that water can be poured in the opening and activate the casting material without having to immerse the device or wet the external surfaces.

In yet another embodiment, the outer liquid containment layer is made of material through which liquid water can pass, a wet sponge, or the like, is rubbed over this surface and forces water through the outer liquid containment layer into the casting material. In all embodiments, immersion of the casting device is not necessary, so that the patient contact side remains dry.

These objects are meant to be illustrative and not limiting. The manner of operation, novel features and further objectives and advantages of this invention may be better understood by reference to the accompanying drawings, description and claims.

BRIEF DESCRIPTION OF THE DRAWINGS

FIG. 1 is a cross sectional view of the device.

FIG. 2 is a perspective view of the device with an open end.

FIG. 3 is a perspective view of the device with a water reservoir therein.

FIG. 4 is a perspective view of the device with a portal.

FIG. 5 is a partial cross sectional view of the device with a water reservoir therein.

FIG. 6 is a cross sectional view of the device with a peelable outer layer.

FIG. 7 is a cross sectional view of the device without additional layers.

FIG. 8 is a perspective view of the device as applied to a forearm as a splint.

DESCRIPTION OF THE PREFERRED EMBODIMENT

Figure 9:
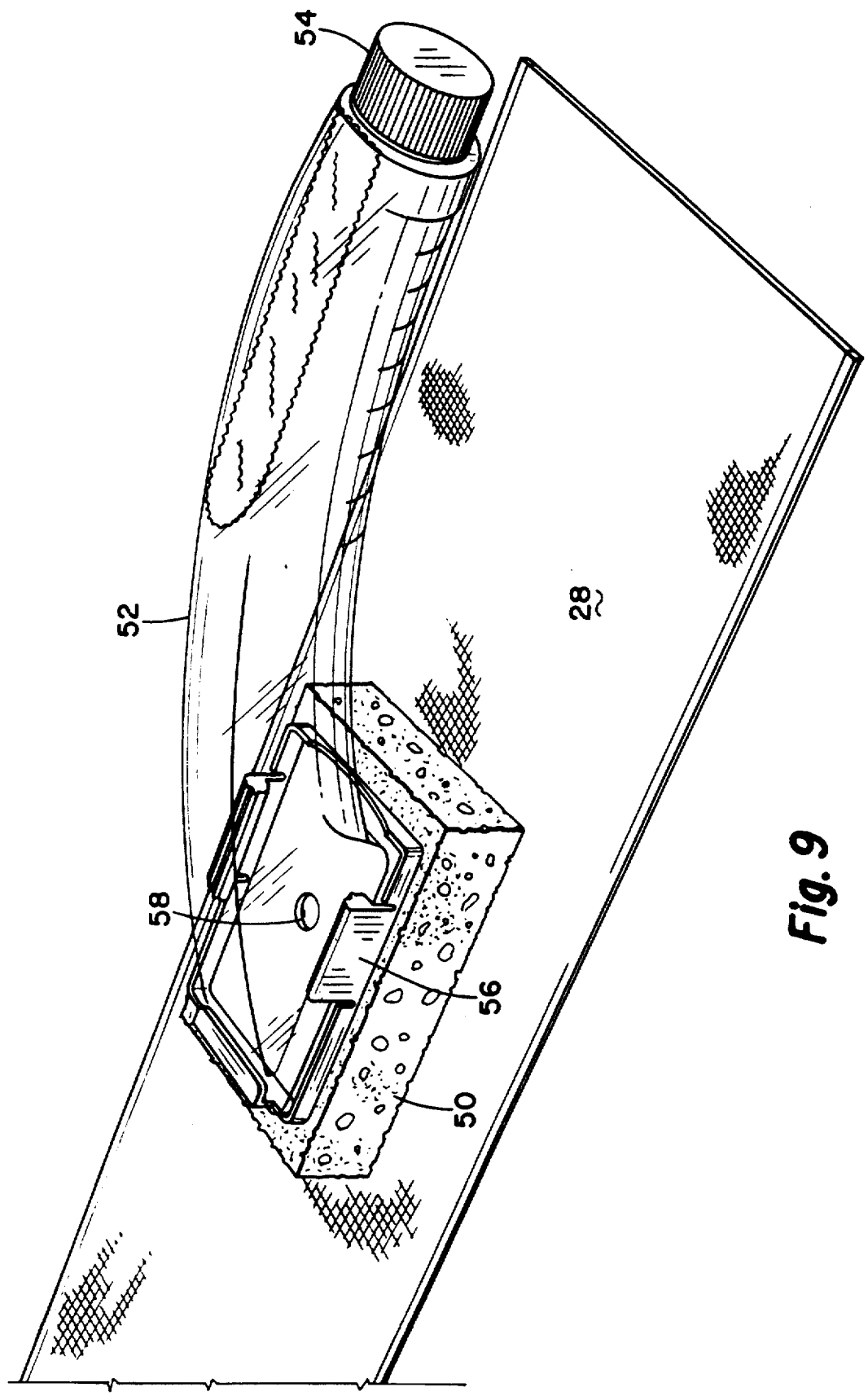
FIG. 9 is a perspective view of the device with a liquid containing sponge applicator being used to apply water to the outer layer.

FIG. 1 illustrates the preferred embodiment of this invention in cross-section. Five (5) layers and a space are illustrated:

1. Patient contact layer 20 formed of closed-cell polyurethane film.
2. Padded layer 22 formed of open-cell polyurethane foam.
3. Inner water containment layer 24 formed of a hydrophobic spun-bonded polypropylene non-woven fabric.
4. Casting member layer 26 made of a substrate coated or impregnated with casting material.
5. Outer water containment layer 28 made of a hydrophobic spun-bonded polypropylene non-woven fabric.
6. Water containment space 30 (a pouch) which is formed between the inner and outer water containment layers, and which contains the casting member layer.

The patient contact layer 20, padded layer 22, inner water containment layer 24, and the outer water containment layer 28 are sealed, or otherwise fastened together, at the periphery 32. The casting material layer 26 is contained, and restrained within the space 30 between the inner 24 and outer 28 water containment layers, but is smaller in outline, so it is not included in the peripheral seal 32.

The patient contact layer 20 is preferably formed of a flexible material that will conform to the patient or workpiece outline and is impervious to liquid water, but which will allow water vapor to pass through it (i.e., having a high moisture vapor transmission). This is the layer that will be in contact with the patient. It is preferable that this layer have a smooth surface that will not cause skin irritation and that it will conform to the patient surface outline. Closed-cell polyurethane film meets these criteria. Open-cell polyurethane foam can also be used. Other suitable materials such as GORETEX TM may also be used.

The padded layer 22 is preferably of a material that will not retain water (non-hydrophilic or substantially hydrophobic), but will allow water vapor to pass through it, and which is padded so that it will conform to the patient or workpiece surface and provides comfort, resiliency and protection. Open-cell polyurethane foam meets these criteria. Other suitable materials may be used.

The inner water containment layer 24 is formed of material that will retain liquid water. This should also allow the passage of water vapor so that moisture does not build up beneath this layer. Spun-bonded hydrophobic polypropylene non-woven fabric meets these criteria. Other suitable materials such as GORETEX ® fabric, polyurethane film, and the like, may be used.

The outer water containment layer 28 is also formed of material that will retain liquid water and allow the passage of water vapor. Spun-bonded hydrophobic polypropylene non-woven fabric meets these criteria. Other suitable materials such as closed-cell polyurethane film, GORETEX ® fabric, or the like, may be used. In the embodiment (described below in FIG. 9) in which water is introduced to the casting member by rubbing a wet sponge (or other water carrying means) over the surface of this layer—this layer is perforated by holes or passages to allow the liquid water from the sponge to pass through the layer and into the pouch so that it can react with the casting member.

The inner water containment layer 24 and the outer water containment layer 28 form, between them, a space 30 which is essentially a pouch that can contain the casting layer 26 and the water used to react with the casting layer 26.

The casting member layer 26 forms the rigid portion of the cast or splint when it has been activated and cured. Polymer resins such as those disclosed in U.S. Pat. Nos. 4,411,262 and 4,502,479 are exemplary of reactive hardenable resins disclosed for use in orthopedic bandages or casting tapes cured with water. See also the teachings of U.S. Pat. No. 4,442,833, all of the above patents being incorporated herein by specific reference. Other casting materials, such as plaster of Paris, or the like may also be used. Casting resins or materials that are activatable by liquids or materials other than water may also be used—the activating material should be non-toxic to the patient. The casting member layer 26 has a support substrate, such as a woven or knitted fabric or mesh, such as fiberglass or other suitable material. This substrate is coated or impregnated with the resin or casting material. It is important that the substrate allow the free passage of water, or activating liquid, to react with the casting material. It is also important that the inner 24 and outer 28 water containment layers retain the liquid within the space 30 so that it can react with the casting material layer 26.

Once the above layers 20, 22, 24, 26, and 28 are assembled in making the device, the edges of the layers 20, 22, 24, and 28 are sealed at the periphery 32 by any suitable means such as heat and pressure, thereby enclosing the casting layer 26 and forming a unitary product or device. It is another feature of the preferred materials (polyurethanes and polypropylenes) used in the layers that they are easily heat and pressure sealed. These layers are slightly larger in outline than the casting member layer 26 so that the sealed periphery will be peripheral to the casting layer 26. Other means of sealing such as adhesives, sewing, clips and the like may be used. Since the product does not use a sheath or other form constricting means, the outline and configuration of the device may be of any shape (as illustrated in application Ser. No. 07/700,555).

Also incorporated into the device is a means of introducing water (or cast activating liquid/material) into the space 30 (of the pouch) so that it can react with the casting member layer 26. Various methods of doing this are illustrated in FIGS. 2 (open end), 3 (water reservoir), 4 (portal), and 9 (water transmissable outer layer).

In FIG. 2 one end of the pouch is left unsealed to provide an opening 36 into which water may be poured to contact the casting member 26. The entire end may be left open, as illustrated here, or only a portion of one edge or end.

FIG. 3 illustrates a water reservoir 38 which is incorporated within the space 30 of the pouch. This water containing reservoir 38 is made of water impervious material, such as plastic, and may be ruptured by pressure, or otherwise opened, to allow the water contained therein to enter the space 30 and react with the casting member 26. This water reservoir embodiment is also shown in cross-section in FIG. 5. In this embodiment, the device is completely self-contained and does not require any exogenous water for use.

FIG. 4 illustrates another embodiment of the device wherein the entire periphery is sealed, but there is a portal 40 in the outer water containment layer 28 through which water may be introduced into the space 30 to react with the casting member 26. This portal 40 may be in the side, on the edge, or any suitable location. It may be a sealable plug through which a needle may be inserted to inject water, it may be a resealable flap, a removable plug, or any other suitable means by which water may be introduced into the device and the integrity of the pouch be maintained.

FIG. 5, as noted above, is similar to FIG. 1 but additionally illustrates, in cross-section, a water reservoir 38 incorporated within the space 30.

FIG. 6 illustrates an alternative embodiment wherein the outer water containment layer 28 is formed of a woven material, or other like material, which freely allows the passage of both water vapor and liquid water. In order to retain water within the space 30 an additional layer 50 is incorporated. This additional layer 50 is water impermeable and is attached to the outer water containment layer 28 by adhesive, or other suitable means, so that it can be peeled off of the outer water containment layer 28 when the casting material has cured, thus allowing greater water movement through the outer layer 28.

FIG. 7 illustrates another embodiment of the device in which there is only a pouch with an inner 24 and outer water containment layers 28 and a casting member 26 incorporated therein. In this embodiment, there is no padded layer and no separate patient contact layer. The pouch walls 24 and 28 may be formed of the same material on both sides, or different materials (as illustrated and discussed in FIG. 6). The pouch may be formed of two layers 24 and 28 sealed together 32 (as illustrated) or the pouch may be manufactured as a preformed unit (not illustrated). In this latter case, additional layers may be fastened to the outer surface of the pouch, as required.

FIG. 8 illustrates the device in use. The device in general 44 is shown forming a splint supporting the forearm 46 and hand 48.

FIG. 9 illustrates another embodiment. In this version, the outer liquid containment layer 28 is formed of a hydophobic fabric, such as non-woven spun bonded polypropylene, which has holes or passages within it through which liquid water may pass. A wetted member, such as a sponge, rag or the like, is then rubbed over the surface of the layer 28 and water is thereby forced through the layer 28 into the unlying casting material 26 and initiates setting setting or curing thereof. In the illustration, FIG. 9, a commercially available applicator is used which comprises a sponge 50, a water containing handle 52, with a cap 54 for filling the handle 52, clips and baseplate 56 which hold the handle 52 in contact with the sponge 50, and a hole 58 in the baseplate 56 through which water in the handle 52 may pass into the sponge 50. One such applicator is made by RUBBERMAID ® and another by Kellogg Brush Mfg., Co., Easthampton, Mass. 01027 called SUDS & SPONGE ® No. 817. The advantages of using an applicator like this is that it the user's hands do not have to contact the device, and the water containing chamber in the the applicator may be pre-filled and prepackaged with the device so that it is immediately ready to use and requires no other water.

In assembling the device, the layers 20, 22, 24, 26, and 28 are stacked in a laminar or tier-like manner, and the edges sealed 32. After forming, the unitary casting device is then sealed in a water impervious container, such as metallic foil or plastic, until ready for use. The unitary casting device may be of various outline shapes. Multiple devices may be attached together to form a roll or strip of devices. Colors, patterns, designs and the like may be incorporated into the device—either in the casting resin, in the casting substrate, or in the walls of the pouch, or combinations thereof.

To use the device, the waterproof wrapping is removed, and the water reservoir 38 is disrupted or emptied to activate the casting layer 26. In the embodiments which do not incorporate a water reservoir, water is added to the pouch either through an open edge 36 through a portal 40, or through the outer layer as illustrated in FIG. 9. The device is then formed to the body part or workpiece which is to be splinted or casted and allowed to set or cure. Multiple devices may be layered together in one application, as needed.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A unitary splint forming device for a patient, comprising:

a patient contact layer formed of polyurethane film, with a first side and a second side;

a padded layer formed of polyurethane foam, with a first side and a second side, wherein said second side of said patient contact layer and said first side of said padded layer are in essentially laminar parallel contact;

an inner water containment layer formed of spun bonded polypropylene non-woven hydrophobic fabric, having a first side and a second side, with said first side thereof being in substantially laminar parallel contact with said second side of said padded layer;

an outer water containment layer formed of spun bonded polypropylene non-woven hydrophobic fabric, having a first side and a second side, with said first side thereof being substantially parallel to and spaced from said second side of said inner water containment layer, forming a space therebetween, and wherein there are perforations in said outer water containment layer whereby liquid water applied to the second side thereof may pass through said layer into said space;

means for fastening said patient layer, padded layer, inner water containment layer and outer water containment layer together; and a casting member formed fiberglass mesh with casting resin impregnated therein positioned in said space between said inner and outer water containment layers.

* * * * *